(12) United States Patent
Yun

(10) Patent No.: US 8,909,340 B2
(45) Date of Patent: Dec. 9, 2014

(54) METHODS AND DEVICES FOR TREATING CONDITIONS ASSOCIATED WITH AUTONOMIC DYSFUNCTION

(75) Inventor: Anthony Joonkyoo Yun, Palo Alto, CA (US)

(73) Assignee: Palo Alto Investors, Palo Alto, CA (US)

( * ) Notice: Subject to any disclaimer, the term of this patent is extended or adjusted under 35 U.S.C. 154(b) by 0 days.

(21) Appl. No.: 13/592,102

(22) Filed: Aug. 22, 2012

(65) Prior Publication Data

US 2013/0053817 A1 Feb. 28, 2013

Related U.S. Application Data

(60) Provisional application No. 61/526,609, filed on Aug. 23, 2011.

(51) Int. Cl.
| | | |
|---|---|---|
| A61N 1/04 | (2006.01) | |
| A61M 5/00 | (2006.01) | |
| A61B 5/145 | (2006.01) | |
| A61B 5/00 | (2006.01) | |
| A61B 5/024 | (2006.01) | |
| A61B 5/11 | (2006.01) | |

(52) U.S. Cl.
CPC .............. *A61M 5/00* (2013.01); *A61B 5/14521* (2013.01); *A61B 5/4035* (2013.01); *A61B 5/02405* (2013.01); *A61B 5/1116* (2013.01); *A61B 5/4238* (2013.01); *A61B 5/4266* (2013.01)
USPC ............................................ 607/40; 604/500

(58) Field of Classification Search
None
See application file for complete search history.

(56) References Cited

U.S. PATENT DOCUMENTS

| | | | |
|---|---|---|---|
| 7,899,527 B2 * | 3/2011 | Yun et al. ........................... 607/2 |
| 2002/0091659 A1 | 7/2002 | Beaulieu et al. | |
| 2004/0249416 A1 | 12/2004 | Yun et al. | |
| 2005/0021092 A1 | 1/2005 | Yun et al. | |
| 2005/0143378 A1 | 6/2005 | Yun et al. | |
| 2005/0143788 A1 | 6/2005 | Yun et al. | |
| 2005/0153885 A1 | 7/2005 | Yun et al. | |
| 2005/0240241 A1 | 10/2005 | Yun et al. | |
| 2005/0256028 A1 | 11/2005 | Yun et al. | |
| 2006/0034847 A1 | 2/2006 | Yun et al. | |
| 2006/0035974 A1 | 2/2006 | Yun et al. | |
| 2006/0069012 A1 | 3/2006 | Yun et al. | |
| 2006/0116721 A1 | 6/2006 | Yun et al. | |
| 2006/0190052 A1 | 8/2006 | Yun et al. | |
| 2006/0200194 A1 | 9/2006 | Yun | |
| 2006/0206149 A1 | 9/2006 | Yun | |
| 2007/0112327 A1 | 5/2007 | Yun et al. | |
| 2007/0208382 A1 | 9/2007 | Yun | |
| 2008/0004596 A1 | 1/2008 | Yun et al. | |
| 2008/0075665 A1 | 3/2008 | Yun | |
| 2008/0226715 A1 | 9/2008 | Cha et al. | |
| 2009/0024176 A1 | 1/2009 | Yun et al. | |
| 2010/0119482 A1 | 5/2010 | Yun et al. | |
| 2010/0144691 A1 | 6/2010 | Yun et al. | |
| 2010/0260669 A1 | 10/2010 | Yun et al. | |
| 2010/0262220 A1 | 10/2010 | Yun | |
| 2010/0280116 A1 | 11/2010 | Yun et al. | |
| 2010/0286734 A1 | 11/2010 | Yun et al. | |
| 2011/0015188 A1 | 1/2011 | Yun et al. | |
| 2011/0029030 A1 | 2/2011 | Yun et al. | |
| 2011/0256097 A1 | 10/2011 | Joonkyoo et al. | |
| 2012/0228176 A1 | 9/2012 | Yun et al. | |
| 2012/0228190 A1 | 9/2012 | Yun et al. | |
| 2012/0228191 A1 | 9/2012 | Yun et al. | |
| 2012/0270876 A1 | 10/2012 | Yun et al. | |

OTHER PUBLICATIONS

Chong et al., "AAEM Practice Topic in Electrodiagnostic Medicine, Technology literature review: Quantitative sensory testing", Muscle Nerve, vol. 29, No. 5, pp. 734-747 (2004).
Illigens et al., "Sweat testing to evaluate autonomic function", Clin Auton Res, vol. 19, pp. 79-87 (2009).
Lamarre-Cliche et al., "The fainting patient: value of the head-upright tilt-table test in adult patients with orthostatic intolerance", vol. 164, No. 3, pp. 372-376 (2001).
Tang et al., "Gastroparesis: Approach, Diagnostic Evaluation, and Management", Dis Mon, vol. 57, No. 2, pp. 74-101 (2011).
Tobin et al., "Comparison of different modalities for detection of small fiber neuropathy", Clinical Neurophysiology, vol. 110, pp. 1909-1912 (1999).

* cited by examiner

*Primary Examiner* — Carl H Layno
*Assistant Examiner* — Ankit Tejani
(74) *Attorney, Agent, or Firm* — Bret E. Field; Bozicevic, Field & Francis LLP

(57) ABSTRACT

Methods and devices treating an autonomic nervous system associated disease condition in a subject are provided. Aspects of the invention include inducing one or more physiological response selected from the group consisting of sweating, gastric emptying, enhanced heart rate variability and enhanced quantitative sensory test responsiveness in a manner sufficient to modify the autonomic nervous system so as to treat the subject for the disease condition. The methods and devices find use in a variety of applications, e.g. in the treatment of subjects suffering from conditions arising from disorders of the autonomic nervous system.

14 Claims, No Drawings

METHODS AND DEVICES FOR TREATING CONDITIONS ASSOCIATED WITH AUTONOMIC DYSFUNCTION

CROSS-REFERENCE TO RELATED APPLICATIONS

Pursuant to 35 U.S.C. §119 (e), this application claims priority to the filing date of U.S. Provisional Patent Application Ser. No. 61/526,609 filed Aug. 23, 2011; the disclosure of which is herein incorporated by reference.

INTRODUCTION

Dysautonomia (autonomic dysfunction) is a broad term that describes any disease or malfunction of the autonomic nervous system. This includes postural orthostatic tachycardia syndrome (POTS), inappropriate sinus tachycardia (IST), vasovagal syncope, mitral valve prolapse dysautonomia, pure autonomic failure, neurocardiogenic syncope (NCS), neurally mediated hypotension (NMH), autonomic instability and a number of lesser-known disorders such as cerebral salt-wasting syndrome.

There is continued interest in the development of new methodologies for treating autonomic dysfunction and related conditions.

SUMMARY

Methods and devices treating an autonomic nervous system associated disease condition in a subject are provided. Aspects of the invention include inducing one or more physiological response selected from the group consisting of sweating, gastric emptying, enhanced heart rate variability and enhanced quantitative sensory test responsiveness in a manner sufficient to modify the autonomic nervous system so as to treat the subject for the disease condition. The methods and devices find use in a variety of applications, e.g. in the treatment of subjects suffering from conditions arising from disorders of the autonomic nervous system.

DETAILED DESCRIPTION

Methods and devices treating an autonomic nervous system associated disease condition in a subject are provided. Aspects of the invention include inducing one or more physiological response selected from the group consisting of sweating, gastric emptying, enhanced heart rate variability and enhanced quantitative sensory test responsiveness in a manner sufficient to modify the autonomic nervous system so as to treat the subject for the disease condition. The methods and devices find use in a variety of applications, e.g. in the treatment of subjects suffering from conditions arising from disorders of the autonomic nervous system.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

In further describing embodiments of the invention, aspects of the methods will be described first, followed by a review of aspects of devices for use in the subject methods, embodiments of applications in which the methods and devices find use, as well as kits for performing methods of the invention.

METHODS

Aspects of the invention include methods of treating a subject having a condition arising from autonomic dysfunction. As reviewed above, autonomic dysfunction, i.e., Dysautonomia, is a malfunction of the autonomic nervous system. As reviewed below, a variety of different diseases may be treated according to methods of the invention.

In practicing methods according to embodiments of the invention, a physiological response is enhanced in a manner sufficient to modify the autonomic nervous system so as to treat the disease condition. By "enhanced" it is meant that the magnitude of the physiological response (examples of which are detailed below) is increased, e.g., by 2-fold or more, such as 5-fold or more, including 10-fold or more, as compared to a suitable control.

The physiological response may vary and in some instances is selected from the group consisting of: sweating, gastric emptying, heart rate variability, ability to rapidly transition from prone to suspended orientation, and quantitative sensory test responsiveness. Each of these physiological responses is now described in greater detail.

In some instances, methods of invention include enhancing sweating of a subject in a manner sufficient to modulate the subject's autonomic nervous system so as to treat the target disease condition. In certain of these embodiments, the methods include inducing sweating in the subject. Sweating may be induced using any convenient protocol. In some instances, the subject is subjected to whole body induction of sweating. In these instances, the entire body of the subject may be subjected to an increased temperature sufficient to induce whole body sweating. For example, the subject may be placed in a temperature controlled chamber and the temperature in the chamber elevated to a temperature sufficient to induce sweating, e.g., to a temperature ranging from 45 to 50° C. Where desired, sweat induction may be monitored in a region of the subject's body or the subject entire body may be evaluated for sweat induction, e.g., via thermoregulatory sweat testing (TST) protocols, e.g., as described in Illigens et al., Clin. Auton. Res. (2009) 19:79-87. Instead of whole body sweat induction, localized sweat induction may be employed. For example, Quantitative Sudomotor Reflex Test (QSART) protocols may be employed to locally induce sweating, wherein a cholinergic agent (such as acetylcholine, pilocarpine or methacholine) is iontophoretically administered to a patient, e.g., the arm of a patient, and sweat induction is measured, e.g., with a hygrometer, e.g., as described in Illigens, supra. As a variation, instead of measuring sweat induction with a hygrometer, moldable materials, e.g., silicone, may be employed, e.g., as described in Illigens, supra. In yet other embodiments, Quantitative Direct and Indirect Axon Reflex Testing (QDIRT) protocols may be employed.

As reviewed above, where the physiological response is sweating, sweating will be enhanced in the subject in a manner sufficient to modulate the autonomic nervous system as desired. In some instances, the sweating is induced in a manner sufficient to achieve a desired parasympathetic activity/sympathetic activity ratio, i.e., a desired balance between parasympathetic activity and sympathetic activity. In certain embodiments the desired ratio is analogous to a parasympathetic activity/sympathetic activity ratio observed in a healthy (i.e., a subject not experiencing an abnormality in the autonomic nervous system), "like" or rather analogous subject, e.g., a healthy human subject ranging in age from about 20 years old to about 25 years old (subjects other than humans will have analogous age ranges). For example, if the subject being treated is a human subject, the parasympathetic activity/sympathetic activity ratio provided by the practice of the subject methods may be analogous to the parasympathetic activity/sympathetic activity ratio observed in a healthy human ranging in age from about 20 years old to about 25 years old.

To achieve the desired autonomic nervous system modulation, sweating may be induced a single time or multiple times. Where a given course of treatment (i.e., predetermined dosing schedule) includes induction of sweating multiple times, sweating may be induced, e.g., as described above, and then the sweat stimulus may be removed, e.g., by cessation of exposure to elevated temperature or cessation of administration of a cholinergic agent. Following cessation stimulus, no additional stimulus is administered to the subject until the next time during the course of treatment when sweating is to be induced. The duration of this period between stimulus application, which may be referred to as a "holiday" period, may vary, but in certain embodiments is 1 day or longer, such as 2 days or longer, including 5 days or longer, 10 days or longer, 15 days, or longer. As such, embodiments of the methods include non-chronic (i.e., non-continuous) application of the stimulus. In certain embodiments, stimulus to the subject is done in an "irregularly irregular" manner. As such, duration of the stimulus application events, as well as duration of holiday periods between such events, varies randomly over the entire course of a treatment (which again is predetermined), or at least a portion thereof. In addition, the variation does not follow any pattern, but instead is random.

In some instances, methods of invention include enhancing gastric emptying of a subject in a manner sufficient to modulate the subject's autonomic nervous system so as to treat the target disease condition. In certain of these embodiments, the methods include inducing gastric in the subject. Gastric emptying, i.e., the movement of food from the stomach to the small intestine, may be induced using any convenient protocol. In some instances, electrical stimulation in the form of gastric neurostimulation may be employed to induce gastric emptying. Devices suitable for use in gastric neurostimulation include, but are not limited to: those described in U.S. Pat. Nos. 7,899,541; 7363,084 and 7,200,443; the disclosures of which are herein incorporated by reference. Alternatively, gastric emptying may be induced via pharmacological protocols, e.g., by administering metoclopramide (Reglan, Maxolon, Clopra), cisapride (Propulsid), erythromycin (E-Mycin, Erythrocin, Ery-Tab, EES) and domperidone (Motilium), etc. Where desired, the induction of gastric emptying may be monitored, e.g., using the protocol described in Tang et al., Dis. Mon. (2011) 57:74-101.

As reviewed above, where the physiological response is gastric emptying, gastric emptying will be enhanced in the subject in a manner sufficient to modulate the autonomic nervous system as desired. In some instances, the gastric emptying is induced in a manner sufficient to achieve a desired parasympathetic activity/sympathetic activity ratio, i.e., a desired balance between parasympathetic activity and sympathetic activity. In certain embodiments the desired ratio is analogous to a parasympathetic activity/sympathetic activity ratio observed in a healthy (i.e., a subject not experiencing an abnormality in the autonomic nervous system), "like" or rather analogous subject, e.g., a healthy human subject ranging in age from about 20 years old to about 25 years old (subjects other than humans will have analogous age ranges). For example, if the subject being treated is a human subject, the parasympathetic activity/sympathetic activity ratio provided by the practice of the subject methods may be analogous to the parasympathetic activity/sympathetic activity ratio observed in a healthy human ranging in age from about 20 years old to about 25 years old.

To achieve the desired autonomic nervous system modulation, gastric emptying may be induced a single time or multiple times. Where a given course of treatment (i.e., predetermined dosing schedule) includes induction of gastric empting multiple times, gastric emptying may be induced, e.g., as described above, and then the stimulus may be removed, e.g., by cessation of application of electrical stimulation or cessation of administration of pharmacological agent. Following cessation of stimulus, no additional stimulus is administered to the subject until the next time during the course of treatment when gastric emptying is to be induced. The duration of this period between stimulus application, which may be referred to as a "holiday" period, may vary, but in certain embodiments is 1 hour or longer, e.g., 2 hours or longer, including 3 hours or longer, e.g., 6 hours or longer, 12 hours or longer, 1 day or longer, such as 2 days or longer, including 5 days or longer, 10 days or longer, 15 days, or longer. As such, embodiments of the methods include non-chronic (i.e., non-continuous) application of the stimulus. In certain embodiments, stimulus to the subject is done in an "irregularly irregular" manner. As such, duration of the stimulus application events, as well as duration of holiday periods between such events, varies randomly over the entire course of a treatment (which again is predetermined), or at least a portion thereof. In addition, the variation does not follow any pattern, but instead is random.

In some instances, methods of invention include enhancing heart rate variability (i.e., variation in interval between heart beats) of a subject in a manner sufficient to modulate the subject's autonomic nervous system so as to treat the target disease condition. Any convenient protocol may be employed for enhancing heart rate variability, where suitable protocols include electrical stimulation protocols, e.g., where an implantable pulse generator is employed to cause heart contraction according to a predetermined protocol that enhances heart rate variability in a desired manner. Enhancement of heart rate variability may be monitored using any convenient protocol, e.g., ECG, blood pressure, and the pulse wave signal derived from a photoplethysmograph (PPG).

As reviewed above, where the physiological response is heart rate variability, heart rate variability will be enhanced in the subject in a manner sufficient to modulate the autonomic nervous system as desired. In some instances, the enhancement of heart rate variability is produced in a manner sufficient to achieve a desired parasympathetic activity/sympathetic activity ratio, i.e., a desired balance between parasympathetic activity and sympathetic activity. In certain embodiments the desired ratio is analogous to a parasympathetic activity/sympathetic activity ratio observed in a healthy (i.e., a subject not experiencing an abnormality in the autonomic nervous system), "like" or rather analogous subject, e.g., a healthy human subject ranging in age from about 20 years old to about 25 years old (subjects other than humans will have analogous age ranges). For example, if the subject being treated is a human subject, the parasympathetic activity/sympathetic activity ratio provided by the practice of the subject methods may be analogous to the parasympathetic activity/sympathetic activity ratio observed in a healthy human ranging in age from about 20 years old to about 25 years old.

To achieve the desired autonomic nervous system modulation, heart rate variability may be enhanced a single time or multiple times. Where a given course of treatment (i.e., predetermined dosing schedule) includes enhancement of heart rate variability multiple times, heart rate variability may be enhanced e.g., as described above, and then the stimulus causing the enhancement in heart rate variability may be removed, e.g., by cessation of application of electrical stimulation. Following cessation of stimulus, no additional stimulus is administered to the subject until the next time during the course of treatment when heart rate variability is to be enhanced. The duration of this period between stimulus application, which may be referred to as a "holiday" period, may vary, but in certain embodiments is 1 hour or longer, e.g., 2 hours or longer, including 3 hours or longer, e.g., 6 hours or longer, 12 hours or longer, 1 day or longer, such as 2 days or longer, including 5 days or longer, 10 days or longer, 15 days, or longer. As such, embodiments of the methods include non-chronic (i.e., non-continuous) application of the stimulus. In certain embodiments, stimulus to the subject is done in an "irregularly irregular" manner. As such, duration of the stimulus application events, as well as duration of holiday periods between such events, varies randomly over the entire course of a treatment (which again is predetermined), or at least a portion thereof. In addition, the variation does not follow any pattern, but instead is random.

In some instances, methods of invention include enhancing the ability of a subject to rapidly transition from prone to suspended orientation in a manner sufficient to modulate the subject's autonomic nervous system so as to treat the target disease condition. In some instances, the ability of a subject to withstand rapid transition from a prone to suspended orientation without experiencing adverse effects, e.g., syncope, is enhanced. Any convenient protocol may be employed for enhancing the ability of the subject to rapidly transition from prone to suspended orientation, where suitable protocols rapid transition from prone to suspended (e.g., 60 to 80°) orientations, e.g., as performed during tilt-table tests, e.g., as described in Cliche & Cusson, CMAJ (2001) 164:372-376. In some instances, pharmacological agents may be employed, e.g., syncope susceptibility agents, such as such as glyceryl trinitrate or isoproterenol.

As reviewed above, where the physiological response is ability to rapidly transition from prone to suspended orientation, ability to rapidly transition from prone to suspended orientation will be enhanced in the subject in a manner sufficient to modulate the autonomic nervous system as desired. In some instances, the enhancement of ability to rapidly transition from prone to suspended orientation is produced in a manner sufficient to achieve a desired parasympathetic activity/sympathetic activity ratio, i.e., a desired balance between parasympathetic activity and sympathetic activity. In certain embodiments the desired ratio is analogous to a parasympathetic activity/sympathetic activity ratio observed in a healthy (i.e., a subject not experiencing an abnormality in the autonomic nervous system), "like" or rather analogous subject, e.g., a healthy human subject ranging in age from about 20 years old to about 25 years old (subjects other than humans will have analogous age ranges). For example, if the subject being treated is a human subject, the parasympathetic activity/sympathetic activity ratio provided by the practice of the subject methods may be analogous to the parasympathetic activity/sympathetic activity ratio observed in a healthy human ranging in age from about 20 years old to about 25 years old.

To achieve the desired autonomic nervous system modulation, ability to rapidly transition from prone to suspended orientation may be enhanced a single time or multiple times. Where a given course of treatment (i.e., predetermined dosing schedule) includes enhancement of ability to rapidly transition from prone to suspended orientation, ability to rapidly transition from prone to suspended orientation variability may be enhanced e.g., as described above, and then the stimulus causing the enhancement in ability to rapidly transition from prone to suspended orientation may be removed, e.g., by cessation of application of electrical stimulation. Following cessation of stimulus, no additional stimulus is administered to the subject until the next time during the course of treatment when heart rate variability is to be enhanced. The duration of this period between stimulus application, which may be referred to as a "holiday" period, may vary, but in certain embodiments is 1 hour or longer, e.g., 2 hours or longer, including 3 hours or longer, e.g., 6 hours or longer, 12 hours or longer, 1 day or longer, such as 2 days or longer, including 5 days or longer, 10 days or longer, 15 days, or longer. As such, embodiments of the methods include non-chronic (i.e., non-continuous) application of the stimulus. In certain embodiments, stimulus to the subject is done in an "irregularly irregular" manner. As such, duration of the stimulus application events, as well as duration of holiday periods between such events, varies randomly over the entire course of a treatment (which again is predetermined), or at least a portion thereof. In addition, the variation does not follow any pattern, but instead is random.

In some instances, methods of invention include enhancing quantitative sensory test (QST) responsiveness of a subject in a manner sufficient to modulate the subject's autonomic nervous system so as to treat the target disease condition. Any convenient protocol may be employed for enhancing QST responsiveness, where suitable protocols include stimulating the subject with a suitable stimulus, e.g., vibration or heat, e.g., as described in Chong and Cros, Muscle Nerve (2004) 29:734-747.

As reviewed above, where the physiological response is QST responsiveness, QST responsiveness will be enhanced in the subject in a manner sufficient to modulate the autonomic nervous system as desired. In some instances, the enhancement of QST responsiveness is produced in a manner sufficient to achieve a desired parasympathetic activity/sympathetic activity ratio, i.e., a desired balance between parasympathetic activity and sympathetic activity. In certain embodiments the desired ratio is analogous to a parasympathetic activity/sympathetic activity ratio observed in a healthy (i.e., a subject not experiencing an abnormality in the autonomic nervous system), "like" or rather analogous subject, e.g., a healthy human subject ranging in age from about 20 years old to about 25 years old (subjects other than humans will have analogous age ranges). For example, if the subject being treated is a human subject, the parasympathetic activity/sympathetic activity ratio provided by the practice of the subject methods may be analogous to the parasympathetic activity/sympathetic activity ratio observed in a healthy human ranging in age from about 20 years old to about 25 years old.

To achieve the desired autonomic nervous system modulation, QST responsiveness may be enhanced a single time or multiple times. Where a given course of treatment (i.e., predetermined dosing schedule) includes enhancement of QST responsiveness multiple times, QST responsiveness may be enhanced e.g., as described above, and then the stimulus causing the enhancement in QST responsiveness may be removed, e.g., by cessation of application of vibration or temperature change. Following cessation of stimulus, no additional stimulus is administered to the subject until the next time during the course of treatment when heart rate variability is to be enhanced. The duration of this period between stimulus application, which may be referred to as a "holiday" period, may vary, but in certain embodiments is 1 hour or longer, e.g., 2 hours or longer, including 3 hours or longer, e.g., 6 hours or longer, 12 hours or longer, 1 day or longer, such as 2 days or longer, including 5 days or longer, 10 days or longer, 15 days, or longer. As such, embodiments of the methods include non-chronic (i.e., non-continuous) application of the stimulus. In certain embodiments, stimulus to the subject is done in an "irregularly irregular" manner. As such, duration of the stimulus application events, as well as duration of holiday periods between such events, varies randomly over the entire course of a treatment (which again is predetermined), or at least a portion thereof. In addition, the variation does not follow any pattern, but instead is random.

UTILITY

The subject methods find use in a variety of applications in which it is desired to treat a subject for a condition, e.g., a condition at least influenced by an abnormality in the subject's autonomic nervous system. In such methods, at least a portion of a subject's autonomic nervous system is modulated in a manner suitable to treat the subject for the condition, e.g., in a manner to increase the parasympathetic activity/sympathetic activity ratio or decrease the parasympathetic activity/sympathetic activity ratio in certain embodiments. As indicated above, in many embodiments of this type of application, the subject methods are employed to treat a condition in the subject in order to achieve a desired therapeutic outcome.

The subject methods find use in the treatment of a variety of different conditions in which an abnormality in a subject's autonomic nervous system exists. By treatment is meant that at least an amelioration of the symptoms associated with the condition afflicting the subject is achieved, where amelioration is used in a broad sense to refer to at least a reduction in the magnitude of a parameter, e.g. symptom, associated with the condition being treated. As such, treatment also includes situations where the condition, or at least symptoms associated therewith, are completely inhibited, e.g. prevented from happening, or stopped, e.g. terminated, such that the subject no longer suffers from the condition, or at least the symptoms that characterize the condition. In certain embodiments, the condition being treated is a disease condition.

A variety of subjects are treatable according to the subject methods. In many embodiments the subjects are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the subjects are humans.

As noted above, abnormalities in a subject's autonomic nervous system include those characterized by an abnormally high parasympathetic activity or abnormally low parasympathetic activity and/or an abnormally high sympathetic activity or abnormally low sympathetic activity. Certain abnormalities may be characterized by having normal activity in one of the systems of the autonomic nervous system (the parasympathetic system or sympathetic system), but which may have abnormal activity in the other system (the parasympathetic system or sympathetic system).

The subject methods find use in the treatment of a variety of different conditions, including, but not limited to: cardiovascular conditions including cardiovascular disease, e.g., atherosclerosis, coronary artery disease, hypertension, hyperlipidemia, eclampsia, pre-eclampsia, cardiomyopathy, volume retention, congestive heart failure, QT interval prolongation, aortic dissection, aortic aneurysm, arterial aneurysm, arterial vasospasm, myocardial infarction, reperfusion syndrome, ischemia, sudden adult death syndrome, arrhythmia, fatal arrythmias, coronary syndromes, coronary vasospasm, sick sinus syndrome, bradycardia, tachycardia, thromboembolic disease, deep vein thrombosis, coagulopathy, disseminated intravascular coagulation ("DIC"), mesenteric ischemia, syncope, venous thrombosis, arterial thrombosis, malignant hypertension, secondary hypertension, primary pulmonary hypertension, secondary pulmonary hypertension, raynaud's, paroxysmal supraventricular tachycardia, and the like; neurodegenerative conditions including neurodegenerative diseases, e.g., Alzheimer's Disease, Pick's Disease, Parkinson's Disease, dementia, delirium, amyotrophic lateral sclerosis, and the like; neuroinflammatory conditions including neuroinflammatory diseases, e.g., viral meningitis, viral encephalitis, fungal meningitis, fungal encephalitis, multiple sclerosis, charcot joint, schizophrenia, myasthenia gravis, and the like; orthopedic inflammatory conditions including orthopedic inflammatory diseases, e.g., osteoarthritis, inflammatory arthritis, regional idiopathic osteoporosis, reflex sympathetic dystrophy, Paget's disease, osteoporosis, antigen-induced arthritis, juvenile chronic arthritis, and the like; lymphoproliferative conditions including lymphoproliferative diseases, e.g., lymphoma, lymphoproliferative disease, Hodgkin's disease, inflammatory pseudomotor of the liver, and the like; autoimmune conditions including automimmune diseases, e.g., Graves disease, raynaud's, hashimoto's, takayasu's disease, kawasaki's diseases, arteritis, scleroderma, CREST syndrome, allergies, dermatitis, Henoch-schlonlein purpura, goodpasture syndrome, autoimmune thyroiditis, myasthenia gravis, Reiter's disease, lupus, and the like; inflammatory conditions, e.g., acute respiratory distress syndrome ("ARDS"), multiple sclerosis, rheumatoid arthritis, juvenile rheumatoid arthritis, juvenile chronic arthritis, migraines, chronic headaches, and the like; infectious diseases, e.g., sepsis, viral and fungal infections, diseases of wound healing, wound healing, tuberculosis, infection, AIDS, human immunodeficiency virus, and the like; pulmonary conditions including pulmonary diseases, e.g., tachypnea, fibrotic lung diseases such as cystic fibrosis and the like, interstitial lung disease, desquamative interstitial pneumonitis, non-specific interstitial pneumonitis, intrapulmonary shunts; lymphocytic interstitial pneumonitis, usual interstitial pneumonitis, idiopathic pulmonary fibrosis, pulmonary edema, aspiration, asphyxiation, pneumothorax, right-to-left shunts, left-to-right shunts, respiratory failure, and the like; transplant-related conditions such as transplant related side effects such as transplant rejection, transplant-related tachycardia, transplant related renal failure, transplant related bowel dysmotility, transplant-related hyperreninemia, and the like; gastrointestinal conditions including gastrointestinal diseases, e.g., hepatitis, xerostomia, bowel mobility, peptic ulcer disease, constipation, ileus, irritable bowel syndrome, post-operative bowel dysmotility, inflammatory bowel disease, typhilitis, cholelethiasis, cholestasis, fecal incontinence, cyclic vomiting syndrome, and the like; endocrine conditions including endocrine diseases, e.g., hypothyroidism, hyperglycemia, diabetes, obesity, syndrome X, insulin resistance, polycystic ovarian syndrome ("PCOS"), and the like; genitourinary conditions including genitourinary diseases, e.g., bladder dysfunction, renal failure, erectile dysfunction, hyperreninemia, hepatorenal syndrome, pulmonary renal syndrome, incontinence, arousal disorder, menopausal mood disorder, premenstrual mood disorder, renal tubular acidosis, pulmonary renal syndrome, and the like; skin conditions including skin diseases, e.g., wrinkles, cutaneous vasculitis, psoriasis, rash; and the like; aging associated conditions including aging associated diseases, e.g., shy dragers, multi-system atrophy, age related inflammation conditions, cancer, aging, and the like; neurologic conditions including neurologic diseases such as epilepsy, depression, schizophrenia, seizures, stroke, insomnia, cerebral vascular accident, transient ischemic attacks, stress, bipolar disorder, concussions, post-concussive syndrome, cerebral vascular vasospasm, central sleep apnea, obstructive sleep apnea, sleep disorders, headaches including chronic headaches, migraines, acute disseminated encephalomyelitis ("ADEM"), and the like; pediatric conditions, including pediatric diseases, e.g., respiratory distress syndrome, sudden infant death syndrome, hirschsprung disease, bronchopulmonary dysplasia, congenital megacolon, ananglionosis, juvenile rheumatoid arthritis, juvenile chronic arthritis, and the like; Th-2 dominant conditions including Th-2 dominant diseases, e.g., typhilitis, osteoporosis, lymphoma, myasthenia gravis, lupus, and the like; conditions, including diseases, that cause hypoxia, hypercarbia, hypercapnia, acidosis, acidemia, Chronic Obstructive Pulmonary Disease ("COPD"), emphysema, any chronic lung disease that causes acidosis, acute pulmonary embolism, sudden adult death syndrome ("SADS"), chronic pulmonary embolism, pleural effusion, cardiogenic pulmonary edema, non-cardiogenic pulmonary edema, acute respiratory distress syndrome (ARDS), neurogenic edema, hypercapnia, acidemia, asthma, renal tubular, asthma, acidosis, chronic lung diseases that cause hypoxia, hypercarbia or hypercapnia, and the like; OB-GYN conditions including OB-GYN diseases, e.g., amniotic fluid embolism, menopausal mood disorders, premenstrual mood disorders, pregnancy-related arrhythmias, fetal stress syndrome, fetal hypoxia, amniotic fluid embolism, gestational diabetes, pre-term labor, cervical incompetence, fetal distress, peripartum maternal mortality, peripartum cardiomyopathy, labor complications, premenstrual syndrome, dysmenorrheal, endometriosis, and the like; sudden death syndromes, e.g., sudden adult death syndrome, sudden infant death syndrome, and the like; menstrual related disorders, e.g., pelvic pain, dysmenorrheal, gastrointestinal disease, nausea, and the like; peripartum and pregnancy related conditions, e.g., peripartum cardiomyopathy, and the like; fibrosis; post-operative recovery conditions such as post-operative pain, post-operative ileus, post-operative fever, post-operative nausea, and the like; post-procedural recovery conditions such as post-procedural pain, post procedural ileus, post-procedural fever, post-procedural nausea, and the like; chronic pain; trauma; hospitalization; glaucoma; male infertility; disorders of thermoregulation; respiratory sinus arrhythmia; VQ mismatch; fibromyalgia; and the like.

Other conditions may also be treated in accordance with the subject invention. Embodiments of the subject invention include treating one or more conditions, sequentially or at the same time, in accordance with the subject invention. Further description of target disease conditions is found in U.S. Pat. No. 7,149,574, and published U.S. patent applications 2005/0021092 and 2005/0240241, incorporated herein by reference.

DEVICES

Aspects of the invention include devices and systems, including a physiological response stimulator, e.g., electrical stimulator, pharmacological agent deliver device, etc., operatively coupled to a controller configured to operate the device in a manner sufficient to enhance a physiological response in a manner sufficient to modify the autonomic nervous system so as to treat the subject for the disease condition, e.g., as described above. The systems of the invention include an implantable device, such as an implantable pulse generator or an implantable pharmacological agent delivery device. Instead of an implantable device, the device may be configured to be stably associated with a topical surface of the subject, e.g., an iontophoretic device. The controller may be any suitable component, and may include a suitable combination of hardware and software.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of treating a subject having a condition arising from autonomic dysfunction, the method comprising:
enhancing one or more physiological responses selected from the group consisting of:
sweating,
gastric emptying,
heart rate variability,
ability to rapidly transition from prone to suspended orientation, and
quantitative sensory test responsiveness,
in a manner sufficient to modify the autonomic nervous system so as to treat the subject for the disease condition
wherein the enhancing one or more physiological responses is performed multiple times during a course of treatment and comprises an application of a stimulus and the duration of the application varies randomly.

2. The method according to claim 1, wherein the physiological response is heart rate variability.

3. The method according to claim 1, wherein the subject is a mammalian subject.

4. The method according to claim 3, wherein the mammalian subject is a human.

5. The method according to claim 1, wherein the method further comprises diagnosing the subject as having an autonomic nervous system condition.

6. A device comprising:
a physiological response stimulator; and
a controller configured to operate the device in a manner sufficient to perform the method according to claim 1.

7. The device according to claim 6, wherein the device is an implantable device.

8. The implantable device according to claim 7, wherein the implantable device is an implantable pulse generator.

9. The implantable device according to claim 7, wherein the implantable device is an implantable active agent delivery device.

10. The device according to claim 6, wherein the device is configured to be stably associated with a topical surface of the subject.

11. The method according to claim 1, wherein the course of treatment comprises a holiday period between the application of the stimulus.

12. The method according to claim 11, wherein the holiday period between the application of the stimulus is 1 hour or longer.

13. The method according to claim 11, wherein the holiday period between the application of the stimulus varies randomly.

14. The method according to claim 1, wherein the disease condition is a cardiovascular condition selected from the group consisting of: atherosclerosis, coronary artery disease, hypertension, hyperlipidemia, eclampsia, pre-eclampsia, cardiomyopathy, volume retention, congestive heart failure, QT interval prolongation, aortic dissection, aortic aneurysm, arterial aneurysm, arterial vasospasm, myocardial infarction, reperfusion syndrome, ischemia, sudden adult death syndrome, arrhythmia, fatal arrythmias, coronary syndromes, coronary vasospasm, sick sinus syndrome, bradycardia, tachycardia, thromboembolic disease, deep vein thrombosis, coagulopathy, disseminated intravascular coagulation ("DIC"), mesenteric ischemia, syncope, venous thrombosis, arterial thrombosis, malignant hypertension, secondary hypertension, primary pulmonary hypertension, secondary pulmonary hypertension, raynaud's, and paroxysmal supraventricular tachycardia.

* * * * *